United States Patent
Srinivasan Natesan et al.

(10) Patent No.: US 11,183,221 B2
(45) Date of Patent: Nov. 23, 2021

(54) SYSTEM AND METHOD FOR PROVIDING DYNAMIC CONTENT

(71) Applicant: KONINKLIJKE PHILIPS N.V., Eindhoven (NL)

(72) Inventors: Anand Srinivasan Srinivasan Natesan, Chennai (IN); Rithesh Sreenivasan, Bangalore (IN); Rajendra Singh Sisodia, Bhopal (IN); Shahin Basheer, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1739 days.

(21) Appl. No.: 14/974,300

(22) Filed: Dec. 18, 2015

(65) Prior Publication Data
US 2016/0180047 A1 Jun. 23, 2016

(51) Int. Cl.
- *G16H 40/63* (2018.01)
- *A61B 5/0205* (2006.01)
- *G11B 27/10* (2006.01)
- *A61B 5/00* (2006.01)
- *G16H 40/67* (2018.01)
- *G16H 30/20* (2018.01)

(52) U.S. Cl.
CPC ............ *G11B 27/105* (2013.01); *A61B 5/743* (2013.01); *G16H 30/20* (2018.01); *G16H 40/63* (2018.01); *G16H 40/67* (2018.01); *A61B 5/02055* (2013.01); *A61B 5/742* (2013.01)

(58) Field of Classification Search
None
See application file for complete search history.

(56) References Cited

U.S. PATENT DOCUMENTS

| | | |
|---|---|---|
| 2001/0053514 A1 | 12/2001 | Doi et al. |
| 2008/0268413 A1* | 10/2008 | Leichner ............... G06F 19/00 434/262 |
| 2008/0276266 A1 | 11/2008 | Huchital et al. |
| 2009/0235312 A1 | 9/2009 | Morad et al. |
| 2010/0122286 A1 | 5/2010 | Begeja et al. |
| 2010/0162343 A1 | 6/2010 | Roberts et al. |

(Continued)

FOREIGN PATENT DOCUMENTS

| | | |
|---|---|---|
| WO | 2007049163 A2 | 5/2007 |
| WO | 2012135058 A2 | 10/2012 |

OTHER PUBLICATIONS

Gobel et al, Serious Games for Health—Personalized Exergames, Oct. 2010, MM '10: Proceedings of the 18th ACM international conference on Multimedia, pp. 1663-1666 (Year: 2010).*

*Primary Examiner* — Gregory Lultschik (57) ABSTRACT

In certain embodiments, a video file may be obtained based on one or more predetermined criteria. Information associated with a user (to which dynamic content derived from at least a video portion of the video file is to be presented) may be obtained. The video file may be processed based on the information associated with the user to determine reference points within the video file. The dynamic content may be generated based on the reference points such that the dynamic content comprises a first video portion of the video file (that corresponds to at least one of the reference points) and additional content related to the first video portion. The dynamic content may be provided for presentation to the user.

15 Claims, 7 Drawing Sheets

(56) References Cited

U.S. PATENT DOCUMENTS

| | | |
|---|---|---|
| 2012/0011109 A1* | 1/2012 | Ambwani .............. G11B 27/28 |
| | | 707/722 |
| 2012/0077175 A1 | 3/2012 | Levisay et al. |
| 2012/0308211 A1 | 12/2012 | Xu et al. |
| 2012/0310670 A1 | 12/2012 | Pruitt |
| 2013/0218565 A1 | 8/2013 | Patel |
| 2013/0294745 A1 | 11/2013 | Xu et al. |
| 2014/0036023 A1 | 2/2014 | Croen et al. |
| 2014/0075295 A1* | 3/2014 | Xu ....................... G06F 17/289 |
| | | 715/243 |
| 2014/0080110 A1 | 3/2014 | Nguyen |
| 2014/0143805 A1 | 5/2014 | Tojo et al. |

\* cited by examiner

FIG. 1

Content Segment 1
00:00:00.000 --> 00:01:00.000
What is chronic heart failure? The heart is a very sophisticated muscular...

Content Segment 2
00:00:01.000 --> 00:02:00.000
What are the causes of heart failure? The commonest causes of heart failure...

Content Segment 3
00:00:02.000 --> 00:03:00.000
Are there different types of heart failure? There are many different types of heart failure and there are many different ways of classifying it...

FIG. 2A

| Time Duration | Content Segment | Identified Keywords | Count of Keywords in Segment |
|---|---|---|---|
| 00:00:00.000 → 00:01:00.000 | 1 | Sophisticated muscular pump ... | 5 |
| 00:01:00.000 → 00:02:00.000 | 2 | Heart failure, muscular pumping action ... | 7 |
| 00:002.000 → 00:03:00.000 | 3 | Vital functions... | 6 |

SYSTEM AND METHOD FOR PROVIDING DYNAMIC CONTENT

CROSS-REFERENCE TO RELATED APPLICATIONS

This application claims priority to Indian Patent Application No. 6459/CHE/2014, filed on Dec. 22, 2014, which is incorporated by reference herein.

FIELD OF THE INVENTION

The invention relates to providing content to a user and, more particularly, to providing specific and more relevant content dynamically to the user.

BACKGROUND OF THE INVENTION

With the advent of technology, home or other remote monitoring of patients has become a feasible, more economical alternative to continuous care at a hospital to facilitate patient compliance with a clinical care plan and to reduce the number of hospital readmissions. Nevertheless, in the home or other remote monitoring scenarios, patients often fail to adhere to their clinical care plans for a number of reasons, including, for instance, lack of understanding of or interest in aspects of their clinical plans. As an example, although videos relevant to a patient's clinical care plan may be presented to the user, the videos may be long in length and may not be customized for the patient, and, as a result, may cause the patient to lose interest in the concepts discussed in the videos or fail to understand the discussed concepts. Thus, such video presentations may fail to help patients comply with their clinical care plans, resulting in a higher probability of hospital readmission. These and other drawbacks exist.

SUMMARY OF THE INVENTION

Aspects of the invention relate to methods, apparatuses, and/or systems for providing dynamic content, such as generation and presentation of dynamic content to a user.

In an embodiment, a system may comprise a computer system that includes one or more physical processors programmed with computer program instructions which, when executed, cause the computer system to: obtain a video file based on one or more predetermined criteria; obtain information associated with a user to which dynamic content derived from at least a video portion of the video file is to be presented; process, based on the information associated with the user, the video file to determine reference points within the video file; generate, based on the reference points, the dynamic content that comprises a first video portion of the video file and additional content related to the first video portion; and provide the dynamic content for presentation to the user. In an embodiment, the system may comprise one or more vital sign monitoring devices communicatively coupled to the computer system, and the computer system may be caused to: obtain, from the vital sign monitoring devices, vital sign information indicating one or more vital signs of the user; and generate the additional content such that the additional content represents the vital sign information. In an embodiment, the computer system may be caused to: segment the video file into video content segments based on the one or more reference points; and generate the dynamic content to comprise a first video content segment of the video content segments and the additional content.

In an embodiment, a method may be implemented by a computer system that comprises one or more physical processors executing computer program instructions which, when executed, perform the method, the method comprising: obtaining a video file based on one or more predetermined criteria; obtaining information associated with a user to which dynamic content derived from at least a video portion of the video file is to be presented; processing, based on the information associated with the user, the video file to determine reference points within the video file; generating, based on the reference points, the dynamic content that comprises a first video portion of the video file and additional content related to the first video portion; and providing the dynamic content for presentation to the user. In an embodiment, the method may comprise: obtaining, from one or more vital sign monitoring devices communicatively coupled to the computer system, vital sign information indicating one or more vital signs of the user; and generating the additional content such that the additional content represents the vital sign information. In an embodiment, the method may comprise: segmenting the video file into video content segments based on the one or more reference points; and generating the dynamic content to comprise a first video content segment of the video content segments and the additional content.

In an embodiment, a system may comprise a computer system that includes one or more physical processors programmed with computer program instructions which, when executed, cause the computer system to: obtain content based on one or more predetermined criteria; obtain information associated with a user to which dynamic content derived from at least a portion of the obtained content is to be presented; process, based on the information associated with the user, the obtained content to determine reference points within the obtained content; generate, based on the reference points, the dynamic content that comprises a first portion of the obtained content and additional content related to the first portion of the obtained content; and provide the dynamic content for presentation to the user. In an embodiment, the system may comprise one or more vital sign monitoring devices communicatively coupled to the computer system, and the computer system may be caused to: obtain, from the one or more vital sign monitoring devices, vital sign information indicating one or more vital signs of the user; and generate the additional content such that the additional content represents the vital sign information. In an embodiment, the computer system may be caused to: segment the obtained content into content segments based on the one or more reference points; and generate the dynamic content to comprise a first content segment of the content segments and the additional content.

In an embodiment, a method may be implemented by a computer system that comprises one or more physical processors executing computer program instructions which, when executed, perform the method, the method comprising: obtaining content based on one or more predetermined criteria; obtaining information associated with a user to which dynamic content derived from at least a portion of the obtained content is to be presented; processing, based on the information associated with the user, the obtained content to determine reference points within the obtained content; generate, based on the reference points, the dynamic content that comprises a first portion of the obtained content and additional content related to the first portion of the obtained content; and provide the dynamic content for presentation to the user. In an embodiment, the method may comprise: obtaining, from one or more vital sign monitoring devices communicatively coupled to the computer system, vital sign information indicating one or more vital signs of the user; and generating the additional content such that the additional content represents the vital sign information. In an embodiment, the method may comprise: segmenting the obtained content into content segments based on the one or more reference points; and generating the dynamic content to comprise a first content segment of the content segments and the additional content.

Various other aspects, features, and advantages of the invention will be apparent through the detailed description of the invention and the drawings attached hereto. It is also to be understood that both the foregoing general description and the following detailed description are exemplary and not restrictive of the scope of the invention. As used in the specification and in the claims, the singular forms of "a", "an", and "the" include plural referents unless the context clearly dictates otherwise. In addition, as used in the specification and the claims, the term "or" means "and/or" unless the context clearly dictates otherwise.

DETAILED DESCRIPTION OF THE INVENTION

In the following description, for the purposes of explanation, numerous specific details are set forth in order to provide a thorough understanding of the embodiments of the invention. It will be appreciated, however, by those having skill in the art that the embodiments of the invention may be practiced without these specific details or with an equivalent arrangement. In other instances, well-known structures and devices are shown in block diagram form in order to avoid unnecessarily obscuring the embodiments of the invention.

Figure 1:
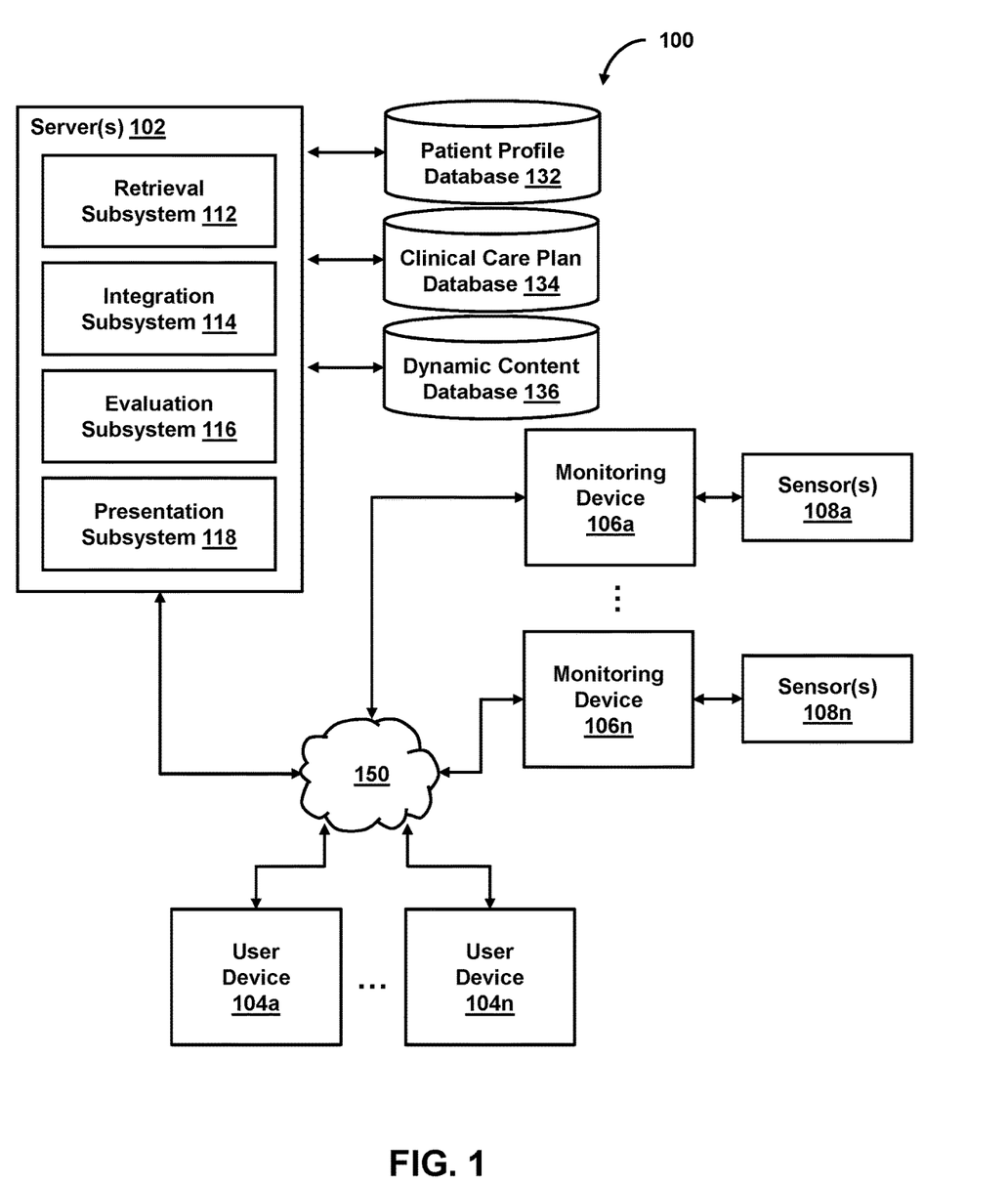
FIG. 1 shows a system for facilitating generation and presentation of dynamic content, in accordance with one or more embodiments.

FIG. 1 shows a system 100 for providing dynamic content, in accordance with one or more embodiments. As shown in FIG. 1, system 100 may comprise server 102 (or multiple servers 102). Server 102 may comprise retrieval subsystem 112, integration subsystem 114, evaluation subsystem 116, presentation subsystem 118, or other components.

System 100 may further comprise user device 104 (or multiple user devices 104a-104n). User device 104 may comprise any type of mobile terminal, fixed terminal, or other device. By way of example, user device 104 may comprise a desktop computer, a notebook computer, a tablet computer, a smartphone, a wearable device, or other user device. In some embodiments, user device 104 may comprise one or more monitoring devices and/or sensors thereof (e.g., monitoring devices 106a-106n, sensors 108a-108n, etc.) for obtaining vital sign information of an individual or other information regarding the user. Users may, for instance, utilize one or more user devices 104 to interact with server 102 or other components of system 100. It should be noted that, while one or more operations are described herein as being performed by components of server 102, those operations may, in some embodiments, be performed by components of user device 104 or other components of system 100.

In some implementations, one or more monitoring devices 106 may be separate and independent from user devices 106 having general functionalities such as those available on common desktop computers, notebook computers, tablet computers, smartphones, etc. The monitoring devices 106 may comprise vital sign monitoring devices, such as insertable cardiac monitors, cardiac event recorders, Holter monitors, heart rate trackers, blood pressure monitors, urine monitoring devices, temperature monitoring devices, saturation measurement devices, blood monitoring devices, or other health monitoring devices. The sensors 106 may comprise oximetry sensors, heart rate sensors, pressure sensors, tactile sensors, glucose sensors, temperature sensors, skin conductance sensors, or other sensors.

Dynamic Content Generation and Presentation

In an embodiment, retrieval subsystem 112 may obtain content based on one or more predetermined criteria (e.g., from clinical care plan database 134 or other database). In an embodiment, retrieval subsystem 112 may obtain information associated with a user (to which dynamic content derived from at least a portion of the obtained content is to be presented). As an example, the obtained content may comprise audio content, video content, or other content. The predetermined criteria may comprise criteria related to an age of the user, an educational background of the user, a cognitive capability level of the user, a social status of the user, a health condition of the user, one or more vital signs of the user, one or more concepts of a clinical care plan of the user, or other criteria. The information associated with the user may comprise the age of the user, the educational background of the user, the cognitive capability level of the user, the social status of the user, the health condition of the user, the vital signs of the user, the concepts of the user's clinical care plan, or other information (e.g., from patent profile database 132, clinical care plan database 134, or other sources).

In an embodiment, integration subsystem 114 may process, based on the information associated with the user, the obtained content to determine reference points within the obtained content. Integration subsystem 114 may generate, based on the reference points, the dynamic content that comprises a first portion of the obtained content and additional content related to the first portion of the obtained content. Presentation subsystem 118 may provide the dynamic content for presentation to the user. In an embodiment, the reference points may comprise locations or portions of the obtained content at which the related additional content may be inserted to generate the dynamic content, locations at which the obtained content may be segmented to create content segments for generating the dynamic content, or other reference points.

As an example, the obtained content may comprise audio or video content, and the dynamic content may comprise a first portion of the audio or video content and the additional content. In one use case, for instance, an audio or video file (comprising the audio or video content) may be obtained based on the file's relevance to a clinical care plan (or concepts or keywords thereof), additionally or alternatively to being based on the file's relevance to an age of a user, an educational background of the user, a cognitive capability level of the user, a social status of the user, a health condition of the user, one or more vital signs of the user, or other aspects of the user. The audio or video file may be utilized along with additional content related to one or more portions of the audio or video file to generate dynamic content that is to be presented to the user. In another use case, the related additional content may be integrated within the audio or video file (e.g., at respective reference points within the file) to generate the dynamic content. In a further use case, the audio or video file may be segmented into content segments (e.g., segmenting at respective reference points within the file), and one or more of the content segments may be included in the dynamic content as part of generating the dynamic content with the related additional content integrated within, adjacent to, or between the included content segments of the dynamic content.

In an embodiment, integration subsystem 114 may determine reference points (e.g., within audio, video, or other content) on which generation of dynamic content may be based. In an embodiment, integration subsystem 114 may determine such reference points by processing the audio, video, or other content for concepts of a clinical care plan or keywords related to such concepts (or the clinical care plan) and selecting the reference points based on identification of concepts or keywords in the audio, video, or other content that corresponds to (e.g., matches or otherwise corresponds to) the plan concepts or keywords. As an example, integration subsystem 114 may process closed caption information of a video file to identify concepts or keywords within the video file, and determine one or more references points for use in generating dynamic content for a user based on the identified concepts or keywords. As another example, integration subsystem 114 may perform speech recognition or natural language processing on the video file to identify concepts or keywords within the video file, and determine one or more such reference points based on the identified concepts or keywords.

In one use case, a reference point may be selected for use in generating dynamic content for a user if the reference point corresponds to a location or a portion of the video file that discusses a concept of the user's clinical care plan (e.g., the reference point may be a start location of a segment discussing a concept selected for the dynamic content, an end location of the segment discussing the concept, an identifier for the segment discussing the concept, etc.). This reference point may, for instance, be utilized as an integration marker to indicate the location or portion of the video file as a place to embed additional content related to the selected concept (e.g., a user's real-time vital sign information related to the concept, the user's patient profile information related to the concept, questionnaires or surveys related to the concept, or other additional content). In another use case, the reference point (and/or other reference points) may be utilized to create segments of the video file (e.g., for dynamic content to be presented to the user), such as a segment of the video file that discusses the selected concept of the user's clinical care plan, another segment of the video file that discusses another concept of the user's clinical care plan, a segment of the video file that contains a minimum and/or maximum number of keywords related to the selected concept, or other segments.

In an embodiment, integration subsystem 114 may determine reference points (e.g., reference points within audio, video, or other content on which generation of dynamic content may be based) by processing the audio, video, or other content for concepts or keywords (and their respective locations) in the audio, video, or other content to identify portions thereof suitable for or relevant to a user (e.g., to which the dynamic content is to be presented). As an example, a reference point may be selected (e.g., for use in generating the dynamic content from a video file) based on the reference point corresponding to a location or portion of the video file that is appropriate for the user's age, the user's educational background, the user's cognitive capability level, the user's health condition, etc. In one scenario, for instance, the reference point (and/or other reference points) may be utilized to leave out portions of the video file that are not appropriate for children (if the user is a child) when generating dynamic content for the user using the video file.

In an embodiment, dynamic content that is provided for presentation to a user may be based on a user's vital signs or other user information, additionally or alternatively to being based on audio or video content (or other content) obtained to generate the dynamic content. As an example, content representing a patient's vital signs may be integrated as part of the dynamic content (that is being or to be presented to the patient) at points within audio or video content (of the dynamic content) related to a clinical care plan for the patient. In this way, because individuals are more likely to be interested in and attentive to aspects about themselves, the dynamic content (with its integration of the patient's own vital signs) may improve patient engagement and increase the efficacy of a patient monitoring system (or other system in which an individual's attention is preferred) when the dynamic content is provided as part of such system.

In an embodiment, retrieval subsystem 112 may obtain vital sign information indicating one or more vital signs of the user from one or more vital sign monitoring devices (e.g., monitoring devices 106). In an embodiment, integration subsystem 114 may utilize the vital sign information to generate content for the dynamic content. The content (generated using the vital sign information) may comprise a visual representation (e.g., graphics, animation, video, etc.) of the vital signs of the user, an audio representation of the vital signs of the user, or other content. As an example, a video file related to a clinical care plan of a patient and the vital signs of the patient may be utilized to generate dynamic content for presentation to the user. Integration subsystem 114 may, for instance, insert one or more visual or audio representations of the patient's vital signs as additional content into respective reference points within the video file that discuss concepts related those vital signs to generate the dynamic content, where the dynamic content comprises at least part of the video file with the inserted visual or audio representations. In one scenario, the portion of the video file of the dynamic content discussing blood pressure may be embedded with a visual or audio representation of the patient's measured blood pressure. In another scenario, the portion of the video file of the dynamic content discussing heart rate may be embedded with a visual or audio representation of the patient's measured heart rate. In yet another scenario, the portion of the video file of the dynamic content discussing body temperature may be embedded with a visual or audio representation of the patient's measured temperature.

In an embodiment, retrieval subsystem 112 may obtain vital sign information (indicating one or more vital signs of a user) from one or more vital sign monitoring devices during a presentation of a first portion of dynamic content to the user. Based on the vital sign information, integration subsystem 114 may generate and insert additional content representing the vital sign information (or the indicated vital signs) into the dynamic content such that a second portion of the dynamic content subsequently presented to the user comprises the inserted additional content (representing the vital sign information). In one use case, while some part of the video file of the dynamic content discussing blood pressure is being presented to a patient, retrieval subsystem 112 may obtain the patient's blood pressure in real-time from a blood pressure monitoring device (monitoring the patient during the presentation of the dynamic content), and integration subsystem 114 may generate and insert a visual or audio representation of the patient's blood pressure in the dynamic content such that the patient's blood pressure may be presented as part of the dynamic content in some part of the dynamic content discussing blood pressure or a part of the dynamic content thereafter. In another use case, while some part of the video file of the dynamic content discussing heart rate is being presented to the patient, retrieval subsystem 112 may obtain the patient's heart rate in real-time from a heart rate tracker (monitoring the patient during the presentation of the dynamic content), and integration subsystem 114 may generate and insert a visual or audio representation of the patient's heart rate in the dynamic content such that the patient's heart rate may be presented as part of the dynamic content in some part of the dynamic content discussing heart rate or a part of the dynamic content thereafter.

In an embodiment, retrieval subsystem 112 may obtain vital sign information (indicating one or more vital signs of a user) from one or more vital sign monitoring devices prior to a presentation of dynamic content to a user. In an embodiment, during a presentation of a first portion of the dynamic content to the user, integration subsystem 114 may generate additional content representing the vital signal information (or the indicated vital signs) such that a second portion of the dynamic content presented to the user (after the first portion of the dynamic content) comprises the inserted additional content (representing the vital sign information). In an embodiment, integration subsystem 114 may generate the additional content (representing the vital sign information) prior to the presentation of the dynamic content. In one use case, for example, vital sign information may be obtained and stored (e.g., in patient profile database 132) for use in a later presentation of dynamic content to the user (e.g., for use in generating visual or audio representations of the vital sign information for inclusion in the dynamic content, or for other uses). In another use case, visual or audio representations of the vital sign information may be generated based on the vital sign information and stored (e.g., in dynamic content database 136) for use in a later presentation of dynamic content to the user. In yet another use case, visual or audio representations of the vital sign information may be generated based on the visual sign information during a presentation of dynamic content to the user (and presented as part of the dynamic content during such presentation).

In an embodiment, dynamic content that is provided for presentation to a user may comprise one or more content segments of audio or video content (or other content) obtained to generated the dynamic content, where the content segments are identified and selected for the dynamic content based on information associated with the user. In an embodiment, retrieval subsystem 112 may obtain content based on one or more predetermined criteria, and obtain the information associated with the user. Integration subsystem 114 may process the obtained content based on the information associated with the user to determine reference points within the obtained content. Integration subsystem 114 may segment the obtained content into content segments based on the reference points, and generate the dynamic content such that the dynamic content comprises a first content segment of the content segments and additional content related to the first content segment.

Figure 2A:
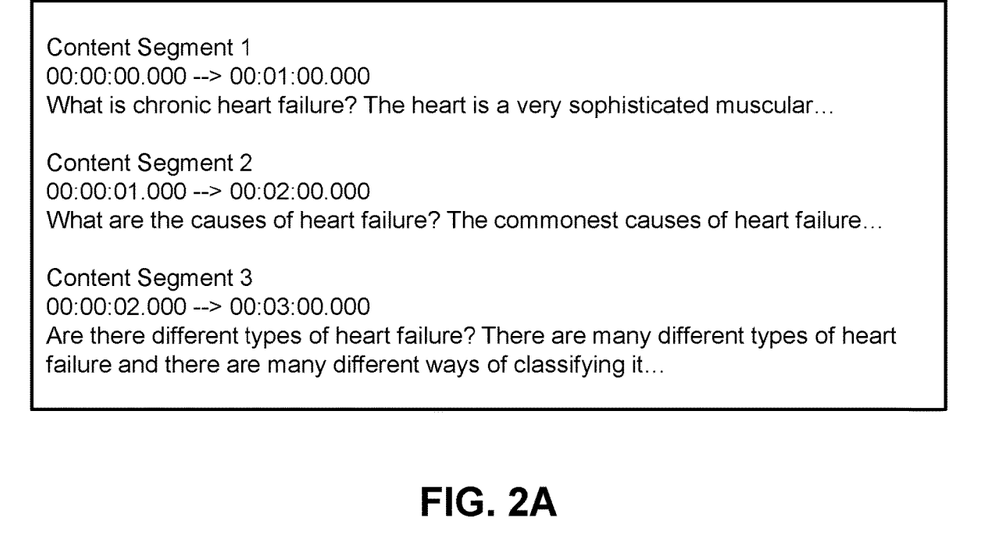
FIGS. 2A and 2B show a table illustrating example closed caption content of a video in content segments of the video and a table illustrating example keyword-based segmentation of the video, respectively, in accordance with one or more embodiments.
Figure 2B:
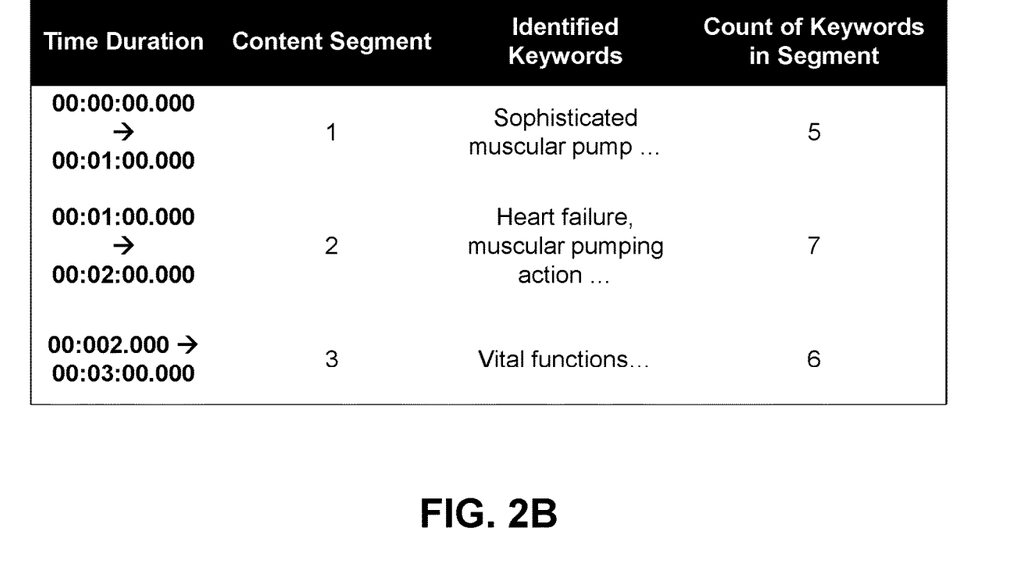

As an example, the information associated with the user may comprise concepts of the user's clinical care plan or keywords related to such concepts, and the reference points within the obtained content (e.g., determined by integration subsystem 114) may be locations or portions of the obtained content that are relevant to those concepts or contains the related keywords (e.g., a start location of a portion discussing a concept, an end location of the portion discussing the concept, etc.). In one use case, with respect to FIGS. 2A and 2B, video content related to a clinical care plan for heart failure patients may be segmented based on the number of keywords related to the clinical care plan, where the number of such keywords in each content segment satisfies a minimum threshold number of keywords and/or satisfies a maximum threshold number of keywords (e.g., 5-7 keywords or other range, only a minimum threshold, only a maximum threshold, etc.). In another use case, with respect to FIG. 2B, dynamic content for a 50-year-old patient with no high school degree and a moderate cognitive capability level may comprise shorter content segments (e.g., derived from a clinical-care-related video) with interactive additional content in between the content segments (e.g., where neither content segments 1, 2, and 3 are continuous in the dynamic content with respect to one another). On the other hand, a 50-year-old patient with a college degree and a high cognitive capability level may comprise longer content segments (e.g., derived from a clinical-care-related video) with interactive additional content in between the content segments (e.g., where content segments 1, 2, and 3 are continuous in the dynamic content with respect to one another).

In an embodiment, upon segmenting obtained content (e.g., an audio or video file or other content) into content segments, integration subsystem 114 may generate content segment files, where each of the content segment files represents one of the content segments. Integration subsystem 114 may generate dynamic content such that the dynamic content comprises a first content segment file of the content segment files, additional content related to the first content segment file, or other content. In a further embodiment, the dynamic content may be generated such that the dynamic content further comprises a second content segment file of the content segment files, additional content related to the second content segment file, or one or more other content segment files (of the content segment file) or their respective related additional content.

In an embodiment, upon segmenting obtained content (e.g., an audio or video file or other content) into content segments, integration subsystem 114 may generate an automated playlist comprising a mechanism to access a first content segment of the content segments, a mechanism to access to additional content related to the first content segment, or other content access mechanisms. In a further embodiment, the automated playlist may be generated such that the automated playlist further comprises a mechanism to access a second content segment of the content segments, a mechanism to access additional content related to the second content segment, or one or more mechanisms to access other content segments (of the content segments) or their respective related additional content. Integration subsystem 114 may generate dynamic content such that the dynamic content comprises the automated playlist, one or more of the content segments, their respective related additional content, or other content. In an embodiment, a next portion of the dynamic content to be presented via the automated playlist may be selected based on the user's understanding of a dynamic content portion presented or being presented to the user, as described in further detail herein. In an embodiment, the automated playlist itself (e.g., as part of the dynamic content) may be configured to assess the user's understanding of a portion presented or being presented to the user and select the next portion of the dynamic content to be presented to the user.

In an embodiment, additional content related to obtained content (or content segments thereof) may comprise one or more related questions, one or more answers to the related questions, or other content. In an embodiment, integration subsystem 114 may obtain one or more questions related to a content segment (of the obtained content) and generate the dynamic content to comprise the content segment and the related questions such that the related questions are presented to the user during presentation of the dynamic content. As an example, the generated dynamic content may be configured such that the related questions may be presented to the user prior to presentation of the content segment (e.g., as a pre-requisite for watching the content segment). As another example, the generated dynamic content may be configured such that the related questions may be presented to the user during presentation of the content segment. As yet another example, the generated dynamic content may be configured such that the related questions may be presented to the user subsequent to presentation of the content segment (e.g., to assess understanding of the materials in the content segment).

In an embodiment, integration subsystem 114 may generate the dynamic content such that the dynamic content is configured to compare one or more user answers obtained during the presentation of the dynamic content with the answers of the dynamic content to evaluate the user answers, and configured to determine a subsequent portion of the dynamic content to be presented to the user based on the evaluation by the dynamic content of the one or more user answers. As an example, the dynamic content may comprise an automated playlist program (or other program) that compares the user answers with the correct answers to assess the user's understanding of a dynamic content portion presented to the user (e.g., the portion of the dynamic content to which the answered questions corresponds). The automated playlist program may then select the next portion of the dynamic content to be presented to the user based on the number of questions that the user answered correctly, the percentages of questions that the user answers correctly in respective question categories, or other criteria. In one use case, if the user fails to correctly answer a threshold number of questions for a first portion of the dynamic content, the first portion of the dynamic content may be repeated or another portion of the dynamic content that helps address lack of understanding of the first portion (e.g., shorter segments, segments with simpler terminology, etc.) may be selected at the next dynamic content portion to be presented to the user. In another use case, if the user correctly answered a threshold number of questions for the first portion of the dynamic content, the automated playlist program may select a portion of the dynamic content that follows chronologically with respect to the audio or video content (or other content) used to generate the dynamic content. In this way, for example, the dynamic content may improve the user's understanding of content presented.

In an embodiment, retrieval subsystem 112 may obtain, during the presentation of dynamic content, one or more user inputs comprising one or more user answers to the questions (of the dynamic content). Upon receipt, evaluation subsystem 116 may evaluate the user answers to the questions. Integration subsystem 114 (or presentation subsystem 118) may determine, based on the evaluation of the one or more user answers, a subsequent portion of the dynamic content to be presented to the user. As an example, the next portion of the dynamic content to be presented to the user may be selected based on the number of questions that the user answered correctly, the percentages of questions that the user answers correctly in respective question categories, or other criteria.

In an embodiment, evaluation subsystem 116 may estimate a clinical outcome with respect to a user based on its evaluation of the user's answers to questions in dynamic content presented to the user. As an example, additionally or alternatively to initial data collected from a patient, evaluation subsystem 116 may assess the number of questions that the patient answered correctly, the percentages of questions that the patient answers correctly in respective question categories, the content segments that was presented to the patient, the number of times each content segment was repeatedly presented (if repeat was needed), the amount of time the patient took to complete the questions, or other criteria to estimate the clinical outcome for the patient. In one use case, if it is determined that the patient understood a video on heart failure diets, it may be estimated that the patient has less questions regarding his/her diet and may not need as many interactions with a caregiver or other personnel on such concept. In another use case, if it is determined that the patient does not understand the video on heart failure diets, suitable alerts and consultation with the caregiver or other personnel would be recommended for the patient.

Examples Flowcharts

FIGS. 3-7 comprise example flowcharts of processing operations of methods that enable the various features and functionality of the system as described in detail above. The processing operations of each method presented below are intended to be illustrative and non-limiting. In some embodiments, for example, the methods may be accomplished with one or more additional operations not described, and/or without one or more of the operations discussed. Additionally, the order in which the processing operations of the methods are illustrated (and described below) is not intended to be limiting.

In some embodiments, the methods may be implemented in one or more processing devices (e.g., a digital processor, an analog processor, a digital circuit designed to process information, an analog circuit designed to process information, a state machine, and/or other mechanisms for electronically processing information). The processing devices may include one or more devices executing some or all of the operations of the methods in response to instructions stored electronically on an electronic storage medium. The processing devices may include one or more devices configured through hardware, firmware, and/or software to be specifically designed for execution of one or more of the operations of the methods.

Figure 3:
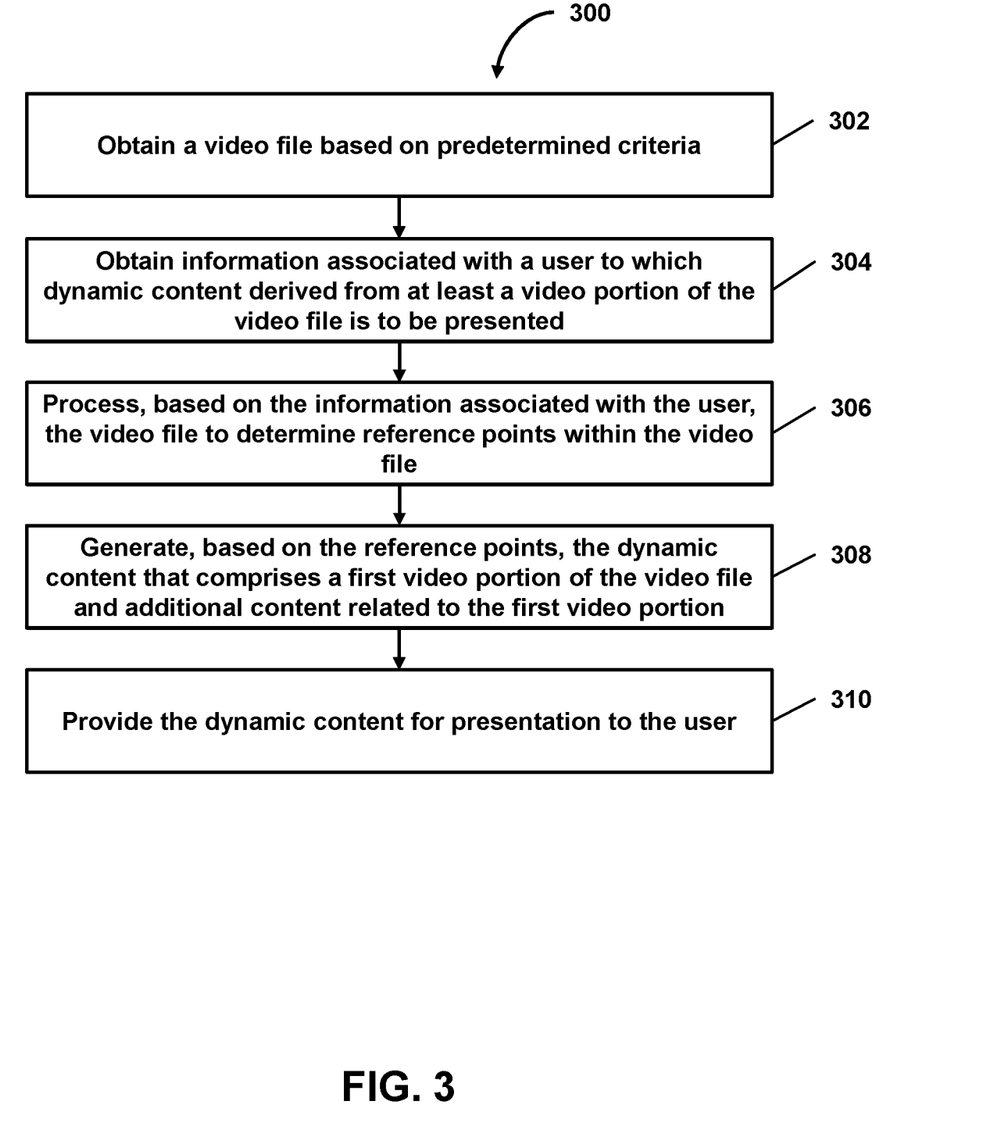
FIG. 3 shows a flowchart of a method of providing dynamic content comprising at least a video portion of a video file and additional content related to the video portion, in accordance with one or more embodiments.

FIG. 3 shows a flowchart of a method 300 of providing dynamic content comprising at least a video portion of a video file and additional content related to the video portion, in accordance with one or more embodiments.

In an operation 302, a video file may be obtained based on one or more predetermined criteria. As an example, the predetermined criteria may comprise information associated with a user, clinical care plan information, or other criteria. Operation 302 may be performed by a retrieval subsystem that is the same as or similar to retrieval subsystem 112, in accordance with one or more embodiments.

In an operation 304, information associated with a user (to which dynamic content derived from at least a video portion of the video file is to be presented) may be obtained. The information associated with the user may comprise an age of the user, an educational background of the user, a cognitive capability level of the user, a social status of the user, a health condition of the user, one or more vital signs of the user, one or more concepts of a clinical care plan of the user, or other information. Operation 304 may be performed by a retrieval subsystem that is the same as or similar to retrieval subsystem 112, in accordance with one or more embodiments.

In an operation 306, the video file may be processed based on the information associated with the user to determine one or more reference points within the video file. As an example, the video file may be processed to determine one or more relevant reference points with respect to the user (e.g., concepts of a clinical care plan of the user or other aspects related to the user). Operation 306 may be performed by an integration subsystem that is the same as or similar to integration subsystem 114, in accordance with one or more embodiments.

In an operation 308, the dynamic content may be generated based on the reference points such that the dynamic content comprises a first video portion of the video file, additional content related to the first video portion, or other content. Operation 308 may be performed by an integration subsystem that is the same as or similar to integration subsystem 114, in accordance with one or more embodiments.

In an operation 310, the dynamic content may be provided for presentation to the user. Operation 310 may be performed by a presentation subsystem that is the same as or similar to presentation subsystem 118, in accordance with one or more embodiments.

Figure 4:
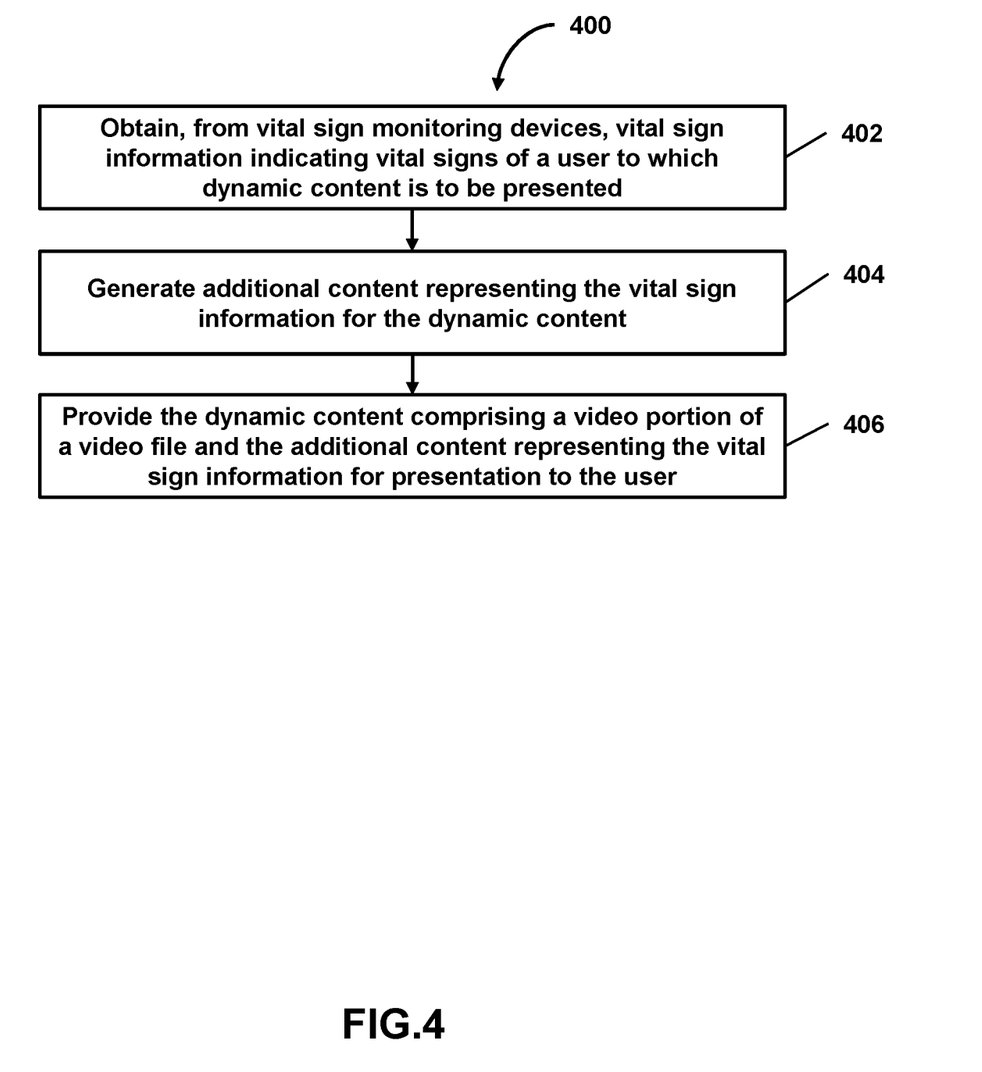
FIG. 4 shows a flowchart of a method of providing dynamic content based on vital sign monitoring of a user such that the dynamic content comprises a video portion of a video file and additional content representing vital sign information derived from the vital sign monitoring, in accordance with one or more embodiments.

FIG. 4 shows a flowchart of a method 400 of providing dynamic content based on vital sign monitoring of a user such that the dynamic content comprises a video portion of a video file and additional content representing vital sign information derived from the vital sign monitoring, in accordance with one or more embodiments.

In an operation 402, vital sign information indicating one or more vital signs of a user (to which dynamic content is to be presented) may be obtained from one or more vital sign monitoring devices. As an example, the vital sign monitoring devices may comprise insertable cardiac monitors, cardiac event recorders, Holter monitors, heart rate trackers, blood pressure monitors, urine monitoring devices, temperature monitoring devices, saturation measurement devices, blood monitoring devices, or other health monitoring devices. The sensors may comprise oximetry sensors, heart rate sensors, pressure sensors, tactile sensors, glucose sensors, temperature sensors, skin conductance sensors, or other sensors. Operation 402 may be performed by a retrieval subsystem that is the same as or similar to retrieval subsystem 112, in accordance with one or more embodiments.

In an operation 404, additional content (representing the vital sign information) for the dynamic content may be generated. As an example, the additional content may comprise a visual representation (e.g., graphics, animation, video, etc.), an audio representation, or other content representative of the vital sign information of the user. Operation 404 may be performed by an integration subsystem that is the same as or similar to integration subsystem 114, in accordance with one or more embodiments.

In an operation 406, the dynamic content (comprising a video portion of a video file and the additional content representing the vital sign information of the user) may be provided for presentation to the user. As an example, the video file (from which the dynamic content is derived) may be obtained for the dynamic content based on one or more predetermined criteria. The predetermined criteria may comprise criteria related to information associated with a user, clinical care plan information, or other criteria. Operation 406 may be performed by an integration subsystem that is the same as or similar to integration subsystem 114, in accordance with one or more embodiments.

Figure 5:
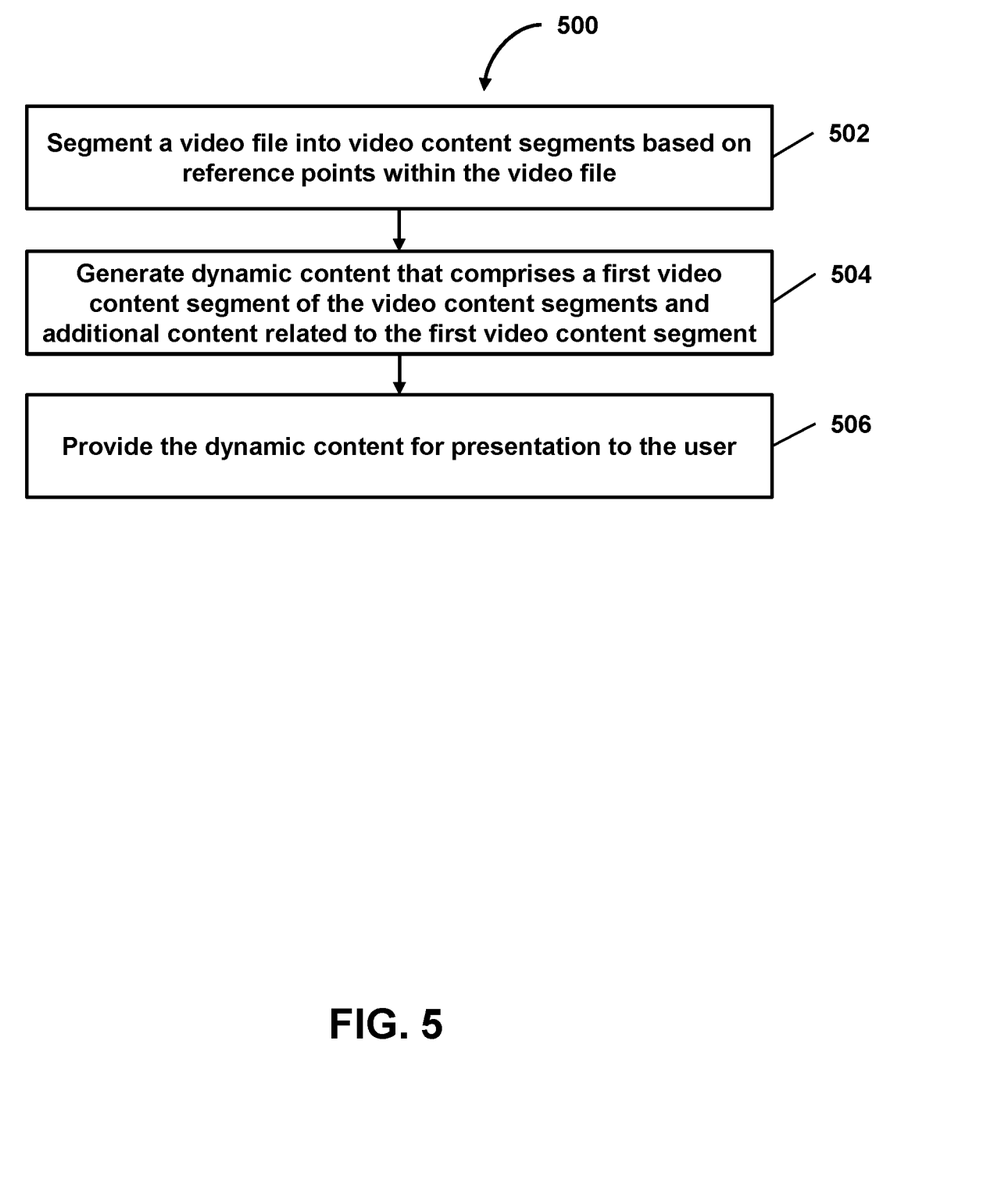
FIG. 5 shows a flowchart of a method of providing dynamic content based on a segmentation of a video file via reference points determined based on information associated with a user, in accordance with one or more embodiments.

FIG. 5 shows a flowchart of a method 500 of providing dynamic content based on a segmentation of a video file via reference points determined based on information associated with a user, in accordance with one or more embodiments.

In an operation 502, a video may be segmented into video content segments based on one or more reference points within the video file. As an example, the video file (from which the dynamic content is derived) may be obtained for the dynamic content based on one or more predetermined criteria. The predetermined criteria may comprise criteria related to information associated with a user, clinical care plan information, or other criteria. As a further example, the reference points may be determined by processing the video file based on information associated with the user, such as an age of the user, an educational background of the user, a cognitive capability level of the user, a social status of the user, a health condition of the user, one or more vital signs of the user, one or more concepts of a clinical care plan of the user, or other information. Operation 502 may be performed by an integration subsystem that is the same as or similar to integration subsystem 114, in accordance with one or more embodiments.

In an operation 504, dynamic content may be generated to comprise a first video content segment (of the video content segments) and additional content related to the first video content segment. As an example, content segment files may be generated such that they each represent one of the video content segments, and the dynamic content may be generated to comprise a first content segment file (of the content segment files that represents the first video content segment) and the additional content. As another example, an automated playlist may be generated to comprise a mechanism to access the first video content segment, a mechanism to access to the additional content, or other mechanism to access other content. Operation 504 may be performed by an integration subsystem that is the same as or similar to integration subsystem 114, in accordance with one or more embodiments.

In an operation 506, the dynamic content may be provided for presentation to the user. Operation 506 may be performed by a presentation subsystem that is the same as or similar to presentation subsystem 118, in accordance with one or more embodiments.

Figure 6:
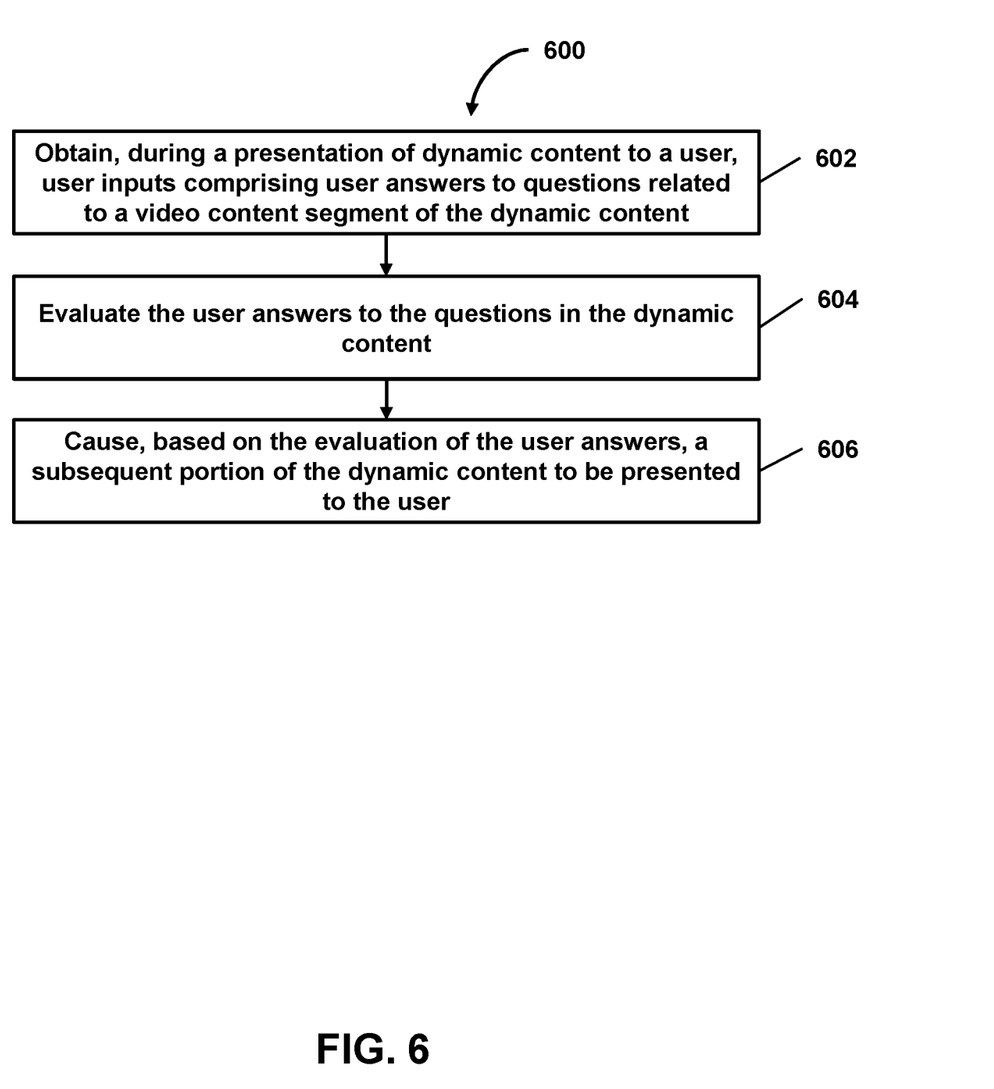
FIG. 6 shows a flowchart of a method of providing dynamic content based on an evaluation of user answers (to questions related to a video content segment of the dynamic content) obtained during a presentation of the dynamic content, in accordance with one or more embodiments.

FIG. 6 shows a flowchart of a method 600 of providing dynamic content based on an evaluation of user answers (to questions related to a video content segment of the dynamic content) obtained during a presentation of the dynamic content, in accordance with one or more embodiments.

In an operation 602, one or more user inputs (comprising one or more user answers to one or more questions related to a video content segment of dynamic content) may be obtained during a presentation of the dynamic content to a user. As an example, the questions may be presented to the user subsequent to a video content segment of the dynamic content (e.g., to test the user's understanding of the concepts discussed in the video content segment after watching the video content segment but before the presentation of a next, undetermined video content segment). Operation 602 may be performed by a retrieval subsystem that is the same as or similar to retrieval subsystem 112, in accordance with one or more embodiments.

In an operation 604, the user answers (to the questions in the dynamic content) may be evaluated. As an example, the user answers may be compared against the correct answers stored in a database to determine one or more scores for the user. Operation 604 may be performed by an evaluation subsystem that is the same as or similar to evaluation subsystem 116, in accordance with one or more embodiments. In an embodiment, the dynamic content itself may store the correct answers to the dynamic content questions, and may be configured to compare the user answers to the correct answers to determine one or more scores for the user.

In an operation 606, a subsequent portion of the dynamic content may be caused to be presented based on the evaluation of the user answers. As an example, the subsequent portion of the dynamic content may be selected as the next portion of the dynamic content to be presented to the user based on the number of questions that the user answered correctly, the percentages of questions that the user answers correctly in respective question categories, or other criteria. In one use case, if the user fails to correctly answer a threshold number of questions for a first portion of the dynamic content, the first portion of the dynamic content may be repeated or another portion of the dynamic content that helps address lack of understanding of the first portion (e.g., shorter segments, segments with simpler terminology, etc.) may be selected at the next dynamic content portion to be presented to the user. Operation 606 may be performed by an integration subsystem or a presentation subsystem that are the same as or similar to integration subsystem 114 or presentation subsystem 118, in accordance with one or more embodiments.

Figure 7:
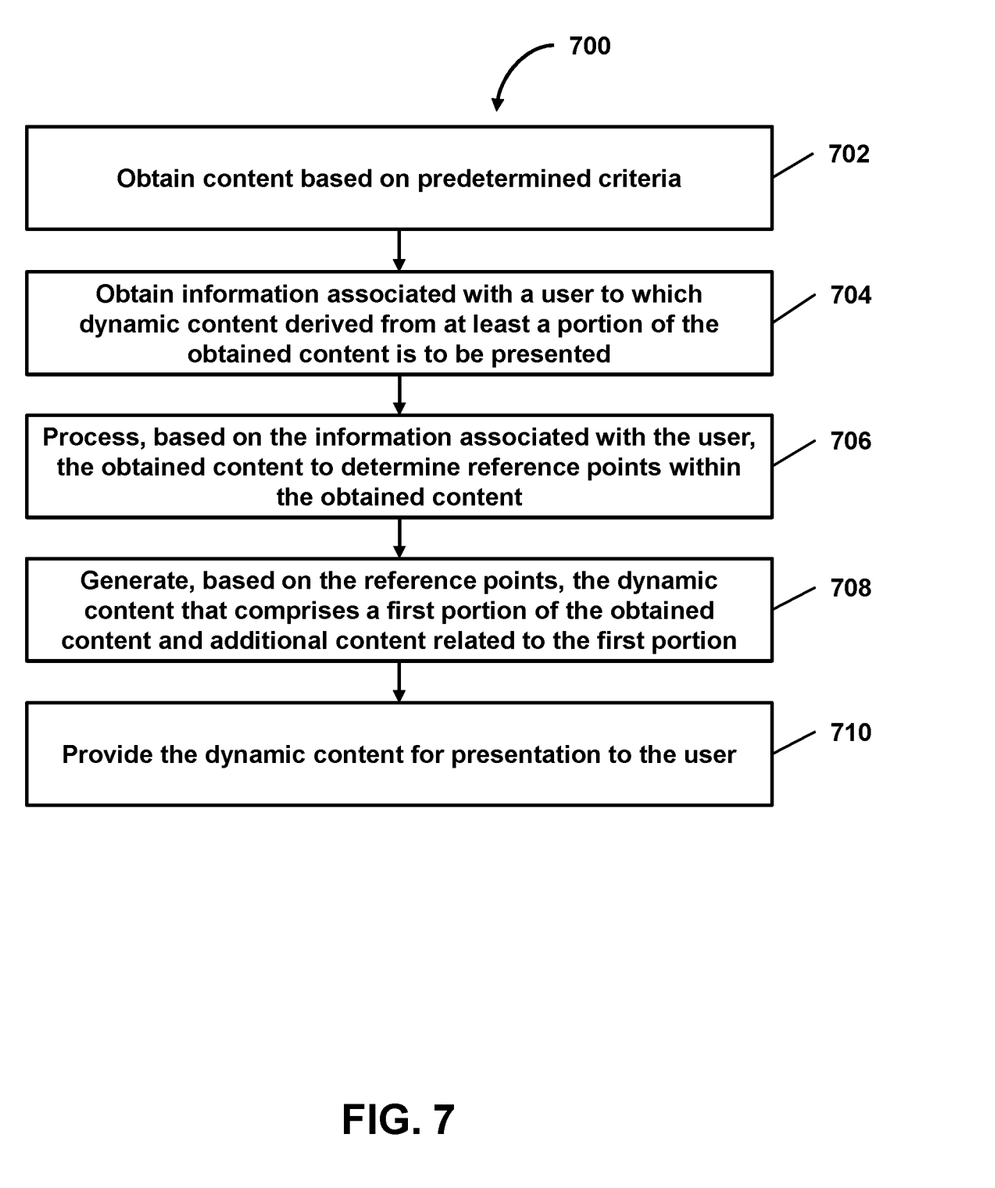
FIG. 7 shows a flowchart of a method of providing dynamic content comprising at least a portion of obtained content and additional content related to the portion of the obtained content, in accordance with one or more embodiments.

FIG. 7 shows a flowchart of a method 700 of providing dynamic content comprising at least a portion of obtained content and additional content related to the portion of the obtained content, in accordance with one or more embodiments.

In an operation 702, content may be obtained based on one or more predetermined criteria. As an example, the predetermined criteria may comprise criteria related to information associated with a user, clinical care plan information, or other criteria. Operation 702 may be performed by a retrieval subsystem that is the same as or similar to retrieval subsystem 112, in accordance with one or more embodiments.

In an operation 704, information associated with a user (to which dynamic content derived from at least a portion of the obtained content is to be presented) may be obtained. The information associated with the user may comprise an age of the user, an educational background of the user, a cognitive capability level of the user, a social status of the user, a health condition of the user, one or more vital signs of the user, one or more concepts of a clinical care plan of the user, or other information. Operation 704 may be performed by a retrieval subsystem that is the same as or similar to retrieval subsystem 112, in accordance with one or more embodiments.

In an operation 706, the obtained content may be processed based on the information associated with the user to determine one or more reference points within the obtained content. As an example, the obtained content may be processed to determine one or more relevant reference points with respect to the user (e.g., concepts of a clinical care plan of the user or other aspects related to the user). Operation 706 may be performed by an integration subsystem that is the same as or similar to integration subsystem 114, in accordance with one or more embodiments.

In an operation 708, the dynamic content may be generated based on the reference points such that the dynamic content comprises a first portion of the obtained content, additional content related to the first portion of the obtained content, or other content. Operation 708 may be performed by an integration subsystem that is the same as or similar to integration subsystem 114, in accordance with one or more embodiments.

In an operation 710, the dynamic content may be provided for presentation to the user. Operation 710 may be performed by a presentation subsystem that is the same as or similar to presentation subsystem 118, in accordance with one or more embodiments.

In some embodiments, the various computers and subsystems illustrated in FIG. 1 may comprise one or more computing devices that are programmed to perform the functions described herein. The computing devices may include one or more electronic storages (e.g., patient profile database 132, clinical care plan database 134, dynamic content database 136, or other electric storages), one or more physical processors programmed with one or more computer program instructions, and/or other components. The computing devices may include communication lines or ports to enable the exchange of information with a network (e.g., network 150) or other computing platforms via wired or wireless techniques (e.g., Ethernet, fiber optics, coaxial cable, WiFi, Bluetooth, near field communication, or other technologies). The computing devices may include a plurality of hardware, software, and/or firmware components operating together to provide the functionality attributed herein to the servers. For example, the computing devices may be implemented by a cloud of computing platforms operating together as the computing devices.

The electronic storages may comprise non-transitory storage media that electronically stores information. The electronic storage media of the electronic storages may include one or both of system storage that is provided integrally (e.g., substantially non-removable) with the servers or removable storage that is removably connectable to the servers via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storage may store software algorithms, information determined by the processors, information received from the servers, information received from client computing platforms, or other information that enables the servers to function as described herein.

The processors may be programmed to provide information processing capabilities in the servers. As such, the processors may include one or more of a digital processor, an analog processor, a digital circuit designed to process information, an analog circuit designed to process information, a state machine, and/or other mechanisms for electronically processing information. In some embodiments, the processors may include a plurality of processing units. These processing units may be physically located within the same device, or the processors may represent processing functionality of a plurality of devices operating in coordination. The processors may be programmed to execute computer program instructions to perform functions described herein of subsystems 112-118 or other subsystems. The processors may be programmed to execute computer program instructions by software; hardware; firmware; some combination of software, hardware, or firmware; and/or other mechanisms for configuring processing capabilities on the processors.

It should be appreciated that the description of the functionality provided by the different subsystems 112-118 described herein is for illustrative purposes, and is not intended to be limiting, as any of subsystems 112-118 may provide more or less functionality than is described. For example, one or more of subsystems 112-118 may be eliminated, and some or all of its functionality may be provided by other ones of subsystems 112-118. As another example, additional subsystems may be programmed to perform some or all of the functionality attributed herein to one of subsystems 112-118.

Example Embodiments

In an embodiment, a system for providing dynamic content may comprise a computer system that comprises one or more physical processors programmed with computer program instructions which, when executed, cause the computer system to: obtain a video file based on one or more predetermined criteria; obtain information associated with a user to which dynamic content derived from at least a video portion of the video file is to be presented; process, based on the information associated with the user, the video file to determine reference points within the video file; generate, based on the reference points, the dynamic content that comprises a first video portion of the video file and additional content related to the first video portion; and provide the dynamic content for presentation to the user.

In an embodiment, wherein the system may comprise one or more vital sign monitoring devices communicatively coupled to the computer system, and wherein the computer system is further caused to: obtain, from the one or more vital sign monitoring devices, vital sign information indicating one or more vital signs of the user; and generate the additional content such that the additional content represents the vital sign information.

In an embodiment, the vital sign information is obtained from the one or more vital monitoring devices during a presentation of a first portion of the dynamic content to the user, and the additional content representing the vital sign information is generated during the presentation of the first portion of the dynamic content, and wherein a second portion of the dynamic content comprising the additional content is presented to the user subsequent to the presentation of the first portion of the dynamic content.

In an embodiment, the vital sign information is obtained from the one or more vital monitoring devices prior to a presentation of the dynamic content to the user. In an embodiment, the additional content representing the vital sign information is generated during a presentation of a first portion of the dynamic content to the user, and wherein a second portion of the dynamic content comprising the additional content is presented to the user subsequent to the presentation of the first portion of the dynamic content. In an embodiment, the additional content representing the vital sign information is generated prior to the presentation of the dynamic content.

In an embodiment, the computer system is further caused to: segment the video file into video content segments based on the one or more reference points, wherein the computer system generates the dynamic content to comprise a first video content segment of the video content segments and the additional content.

In an embodiment, the computer system is further caused to: generate content segment files, each of the content segment files representing one of the video content segments, wherein the computer system generates the dynamic content to comprise a first content segment file of the content segment files and the additional content, the first content segment file representing the first video content segment.

In an embodiment, the computer system is further caused to: generate an automated playlist comprising a mechanism to access the first video content segment and a mechanism to access to the additional content, wherein the computer system generates the dynamic content to comprise the automated playlist, the first video content segment, and the additional content.

In an embodiment, the additional content comprises one or more questions related to at least one of the video content segments in the dynamic content such that the dynamic content is generated to comprise the first video content segment and the one or more questions.

In an embodiment, the additional content comprises the one or more questions and one or more answers to the one or more questions such that the dynamic content is generated to comprise the first video content segment, the one or more questions, and the one or more answers.

In an embodiment, the dynamic content is configured to compare one or more user answers obtained during the presentation of the dynamic content with the one or more answers of the dynamic content to evaluate the one or more user answers, and configured to determine a subsequent portion of the dynamic content to be presented to the user based on the evaluation by the dynamic content of the one or more user answers.

In an embodiment, the computer system is further caused to: obtain, during the presentation of the dynamic content, one or more user inputs comprising one or more user answers to the one or more questions; evaluate the one or more user answers to the one or more questions; and cause, based on the evaluation of the one or more user answers, a subsequent portion of the dynamic content to be presented to the user.

In an embodiment, the computer system is further caused to: modify, based on the evaluation of the one or more user answers, the dynamic content to add or remove content from the dynamic content.

In an embodiment, the computer system is further caused to: determine, based on the evaluation of the one or more user answers, whether the one or more user answers satisfy a threshold amount of correct answers to the one or more questions, wherein the computer system determines the subsequent portion of the dynamic content to be presented based on whether the one or more user answers satisfy the threshold amount of correct answers.

In an embodiment, a method of providing dynamic content may be implemented by a computer system that comprises one or more physical processors executing computer program instructions which, when executed, perform the method. The method may comprise: obtaining a video file based on one or more predetermined criteria; obtaining information associated with a user to which dynamic content derived from at least a video portion of the video file is to be presented; processing, based on the information associated with the user, the video file to determine reference points within the video file; generating, based on the reference points, the dynamic content that comprises a first video portion of the video file and additional content related to the first video portion; and providing the dynamic content for presentation to the user.

In an embodiment, the method may comprise: obtaining, from one or more vital sign monitoring devices communicatively coupled to the computer system, vital sign information indicating one or more vital signs of the user; and generating the additional content such that the additional content represents the vital sign information.

In an embodiment, the vital sign information is obtained from the one or more vital monitoring devices during a presentation of a first portion of the dynamic content to the user, and the additional content representing the vital sign information is generated during the presentation of the first portion of the dynamic content, and wherein a second portion of the dynamic content comprising the additional content is presented to the user subsequent to the presentation of the first portion of the dynamic content.

In an embodiment, the method may comprise: segmenting the video file into video content segments based on the one or more reference points, wherein the dynamic content is generated to comprise a first video content segment of the video content segments and the additional content.

In an embodiment, the method may comprise: generating content segment files, each of the content segment files representing one of the video content segments, wherein the dynamic content is generated to comprise a first content segment file of the content segment files and the additional content, the first content segment file representing the first video content segment.

In an embodiment, the method may comprise: generating an automated playlist comprising a mechanism to access the first video content segment and a mechanism to access to the additional content, wherein the dynamic content is generated to comprise the automated playlist, the first video content segment, and the additional content.

In an embodiment, the additional content comprises one or more questions related to at least one of the video content segments in the dynamic content such that the dynamic content is generated to comprise the first video content segment and the one or more questions.

In an embodiment, the additional content comprises the one or more questions and one or more answers to the one or more questions such that the dynamic content is generated to comprise the first video content segment, the one or more questions, and the one or more answers, and wherein the dynamic content is configured to compare one or more user answers obtained during the presentation of the dynamic content with the one or more answers of the dynamic content to evaluate the one or more user answers, and configured to determine a subsequent portion of the dynamic content to be presented to the user based on the evaluation by the dynamic content of the one or more user answers.

In an embodiment, the method comprises: obtaining, during the presentation of the dynamic content, one or more user inputs comprising one or more user answers to the one or more questions; evaluating the one or more user answers to the one or more questions; and causing, based on the evaluation of the one or more user answers, a subsequent portion of the dynamic content to be presented to the user.

In an embodiment, a system for providing dynamic content may comprise a computer system that comprises one or more physical processors programmed with computer program instructions which, when executed, cause the computer system to: obtain content based on one or more predetermined criteria; obtain information associated with a user to which dynamic content derived from at least a portion of the obtained content is to be presented; process, based on the information associated with the user, the obtained content to determine reference points within the obtained content; generate, based on the reference points, the dynamic content that comprises a first portion of the obtained content and additional content related to the first portion of the obtained content; and provide the dynamic content for presentation to the user.

In an embodiment, the system comprises one or more vital sign monitoring devices communicatively coupled to the computer system, and wherein the computer system is further caused to: obtain, from the one or more vital sign monitoring devices, vital sign information indicating one or more vital signs of the user; and generate the additional content such that the additional content represents the vital sign information.

In an embodiment, the computer system is further caused to: segment the obtained content into content segments based on the one or more reference points, wherein the computer system generates the dynamic content to comprise a first content segment of the content segments and the additional content.

In an embodiment, the computer system is further caused to: generate content segment files, each of the content segment files representing one of the content segments, wherein the computer system generates the dynamic content to comprise a first content segment file of the content segment files and the additional content, the first content segment file representing the first video content segment.

In an embodiment, the computer system is further caused to: generate an automated playlist comprising a mechanism to access the first content segment and a mechanism to access to the additional content, wherein the computer system generates the dynamic content to comprise the automated playlist, the first content segment, and the additional content.

In an embodiment, the additional content comprises one or more questions related to at least one of the content segments in the dynamic content such that the dynamic content is generated to comprise the first content segment and the one or more questions.

In an embodiment, the additional content comprises the one or more questions and one or more answers to the one or more questions such that the dynamic content is generated to comprise the first content segment, the one or more questions, and the one or more answers, and wherein the dynamic content is configured to compare one or more user answers obtained during the presentation of the dynamic content with the one or more answers of the dynamic content to evaluate the one or more user answers, and configured to determine a subsequent portion of the dynamic content to be presented to the user based on the evaluation by the dynamic content of the one or more user answers.

In an embodiment, the computer system is further caused to: obtain, during the presentation of the dynamic content, one or more user inputs comprising one or more user answers to the one or more questions; evaluate the one or more user answers to the one or more questions; and determine, based on the evaluation of the one or more user answers, a subsequent portion of the dynamic content to be presented to the user.

In an embodiment, a method of providing dynamic content may be implemented by a computer system that comprises one or more physical processors executing computer program instructions which, when executed, perform the method. The method may comprise: obtaining content based on one or more predetermined criteria; obtaining information associated with a user to which dynamic content derived from at least a portion of the obtained content is to be presented; processing, based on the information associated with the user, the obtained content to determine reference points within the obtained content; generating, based on the reference points, the dynamic content that comprises a first portion of the obtained content and additional content related to the first portion of the obtained content; and providing the dynamic content for presentation to the user.

In an embodiment, the method may comprise: obtaining, from one or more vital sign monitoring devices communicatively coupled to the computer system, vital sign information indicating one or more vital signs of the user; and generating the additional content such that the additional content represents the vital sign information.

In an embodiment, the method may comprise: segmenting the obtained content into content segments based on the one or more reference points, wherein the dynamic content is generated to comprise a first content segment of the content segments and the additional content.

In an embodiment, the method may comprise: generating content segment files, each of the content segment files representing one of the content segments, wherein the dynamic content is generated to comprise a first content segment file of the content segment files and the additional content, the first content segment file representing the first video content segment.

In an embodiment, the method may comprise: generating an automated playlist comprising a mechanism to access the first content segment and a mechanism to access to the additional content, wherein the dynamic content is generated to comprise the automated playlist, the first content segment, and the additional content.

In an embodiment, the additional content comprises one or more questions related to at least one of the content segments in the dynamic content such that the dynamic content is generated to comprise the first content segment and the one or more questions.

In an embodiment, the additional content comprises the one or more questions and one or more answers to the one or more questions such that the dynamic content is generated to comprise the first content segment, the one or more questions, and the one or more answers, and wherein the dynamic content is configured to compare one or more user answers obtained during the presentation of the dynamic content with the one or more answers of the dynamic content to evaluate the one or more user answers, and configured to determine a subsequent portion of the dynamic content to be presented to the user based on the evaluation by the dynamic content of the one or more user answers.

In an embodiment, the method may comprise: obtaining, during the presentation of the dynamic content, one or more user inputs comprising one or more user answers to the one or more questions; evaluating the one or more user answers to the one or more questions; and determining, based on the evaluation of the one or more user answers, a subsequent portion of the dynamic content to be presented to the user.

Although the present invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the scope of the appended claims. For example, it is to be understood that the present invention contemplates that, to the extent possible, one or more features of any embodiment can be combined with one or more features of any other embodiment.

What is claimed is:

1. A system for providing dynamic content, the system comprising:

a computer system that comprises one or more vital sign monitoring devices communicatively coupled to the computer system and one or more physical processor programmed with computer program instructions which, when executed, cause the computer system to:

obtain a video file based on one or more predetermined criteria;

obtain information associated with a user to which dynamic content derived from at least a video portion of the video file is to be presented;

process, based on the information associated with the user, the video file to determine one or more reference points within the video file;

select video content segments from the video file based on the one or more reference points such that a first video content segment of the video file is selected and a second video content segment of the video file is not selected;

obtain, from the one or more vital sign monitoring devices, vital sign information indicating one or more vital signs of the user;

generate, based on the selection and the vital sign information, the dynamic content that comprises the first video content segment and additional content related to the first video content segment, wherein the additional content indicates the vital sign information; and     provide the dynamic content for presentation to the user, wherein the vital sign information is obtained during a presentation of a first portion of the dynamic content to the user, and the additional content representing the vital sign information is generated during the presentation of the first portion of the dynamic content, and wherein a second portion of the dynamic content comprising the additional content is presented to the user subsequent to the presentation of the first portion of the dynamic content.

2. The system of claim 1, wherein the vital sign information is obtained from the one or more vital monitoring devices prior to a presentation of the dynamic content to the user.

3. The system of claim 2, wherein the additional content representing the vital sign information is generated during a presentation of a first portion of the dynamic content to the user, and wherein a second portion of the dynamic content comprising the additional content is presented to the user subsequent to the presentation of the first portion of the dynamic content.

4. The system of claim 2, wherein the additional content representing the vital sign information is generated prior to the presentation of the dynamic content.

5. The system of claim 1, wherein the computer is further caused to:
generate content segment files, each of the content segment files representing one of the video content segments,
wherein the computer system generates the dynamic content to comprise a first content segment file of the content segment files and the additional content, the first content segment file representing the first video content segment.

6. The system of claim 1, wherein the computer system is further caused to:
generate an automated playlist comprising a mechanism to access the first video content segment and a mechanism to access to the additional content,
wherein the computer system generates the dynamic content to comprise the automated playlist, the first video content segment, and the additional content.

7. The system of claim 1, wherein the additional content comprises one or more questions related to at least one of the video content segments in the dynamic content such that the dynamic content is generated to comprise the first video content segment and the one or more questions.

8. The system of claim 7, wherein the additional content comprises the one or more questions and one or more answers to the one or more questions such that the dynamic content is generated to comprise the first video content segment, the one or more questions, and the one or more answers.

9. The system of claim 8, wherein the dynamic content is configured to compare one or more user answers obtained during the presentation of the dynamic content with the one or more answers of the dynamic content to evaluate the one or more user answers, and configured to determine a subsequent portion of the dynamic content to be presented to the user based on the evaluation by the dynamic content of the one or more user answers.

10. The system of claim 7, wherein the computer system is further caused to:
obtain, during the presentation of the dynamic content, one or more user inputs comprising one or more user answers to the one or more questions;
evaluate the one or more user answers to the one or more questions; and
cause, based on the evaluation of the one or more user answers, a subsequent portion of the dynamic content to be presented to the user.

11. The system of claim 1, wherein the information associated with the user comprises an age of the user, an educational background of the user, a cognitive capability level of the user, a health condition of the user, or one or more vital signs of the user.

12. The system of claim 1, wherein the information associated with the user comprises one or more concepts of a clinical care plan of the user.

13. The system of claim 1, wherein the one or more predetermined criteria comprises criteria related to an age of the user, an educational background of the user, a cognitive capability level of the user, a health condition of the user, one or more vital signs of the user, or one or more concepts of a clinical care plan of the user.

14. A method of providing dynamic content, the method being implemented by a computer system that comprises one or more physical processors executing computer program instructions which, when executed, perform the method, the method comprising:
obtaining a video file based on one or more predetermined criteria;
obtaining information associated with a user to which dynamic content derived from at least a video portion of the video file is to be presented;
processing, based on the information associated with the user, the video file to determine reference points within the video file;
generating, based on the reference points, the dynamic content that comprises a first video portion of the video file and additional content related to the first video portion;
providing the dynamic content for presentation to the user;
obtaining, from one or more vital sign monitoring devices communicatively coupled to the computer system, vital sign information indicating one or more vital signs of the user during a presentation of a first portion of the dynamic content to the user; and
generating the additional content such that the additional content represents the vital sign information, and wherein the additional content is generated during the presentation of the first portion of the dynamic content to the user, and wherein a second portion of the dynamic content comprising the additional content is presented to the user subsequent to the presentation of the first portion of the dynamic content.

15. The method of claim 14, further comprising:
segmenting the video file into video content segments based on the reference points,
wherein the dynamic content is generated to comprise a first video content segment of the video content segments and the additional content.

* * * * *